US012642471B2

(12) United States Patent
Li et al.

(10) Patent No.: US 12,642,471 B2
(45) Date of Patent: Jun. 2, 2026

(54) FLEXIBLE ELECTRODE FOR PERIPHERAL NERVE AND METHOD FOR MANUFACTURING SAME

(71) Applicant: SHANGHAI STAIRMED TECHNOLOGY CO., LTD., Shanghai (CN)

(72) Inventors: Xue Li, Shanghai (CN); Zhengtuo Zhao, Shanghai (CN); Xiaocheng Li, Shanghai (CN)

(73) Assignee: SHANGHAI STAIRMED TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 18/874,487

(22) PCT Filed: Jun. 29, 2022

(86) PCT No.: PCT/CN2022/102335
§ 371 (c)(1),
(2) Date: Dec. 12, 2024

(87) PCT Pub. No.: WO2023/240693
PCT Pub. Date: Dec. 21, 2023

(65) Prior Publication Data
US 2025/0375140 A1 Dec. 11, 2025

(30) Foreign Application Priority Data
Jun. 17, 2022 (CN) ......................... 202210689969.9

(51) Int. Cl.
*A61B 5/294* (2021.01)
*A61B 5/00* (2006.01)
(Continued)

(52) U.S. Cl.
CPC .............. *A61B 5/294* (2021.01); *A61B 5/263* (2021.01); *A61B 5/6877* (2013.01);
(Continued)

(58) Field of Classification Search
CPC ......... A61B 5/263; A61B 5/294; A61B 5/388; A61B 5/6877; A61B 2562/0209; A61N 1/0556
See application file for complete search history.

(56) References Cited

U.S. PATENT DOCUMENTS

2006/0173263 A1    8/2006  He et al.
2014/0148886 A1* 5/2014  Tsang ................... A61N 1/0551
                                 607/118
(Continued)

FOREIGN PATENT DOCUMENTS

CN        1911470 A    2/2007
CN    101172184 A    5/2008
(Continued)

OTHER PUBLICATIONS

Notice of Allowance from Chinese Patent Application No. 202210689969.9 dated Sep. 26, 2024.
(Continued)

*Primary Examiner* — Eun Hwa Kim
(74) *Attorney, Agent, or Firm* — GREENBERG TRAURIG, LLP

(57) ABSTRACT

The present disclosure relates to a flexible electrode for a peripheral nerve and a method for manufacturing the same. A flexible electrode for a peripheral nerve is provided, which includes an implantation portion that can be implanted into a truncated peripheral nerve or a nerve stump and configured to acquire or apply an electrical signal inside and on a surface of a peripheral nerve bundle. The flexible electrode includes first and second insulating layers and a wire layer
(Continued)

100 located therebetween. The implantation portion includes one or more electrode sites each electrically coupled to one of wires in the wire layer and in contact with the peripheral nerve after implantation of the flexible electrode. The implantation portion has pores to facilitate reconstruction of the peripheral nerve and to be in close contact with the peripheral nerve after reconstruction.

20 Claims, 13 Drawing Sheets

(51) Int. Cl.
    *A61B 5/263*        (2021.01)
    *A61N 1/05*         (2006.01)

(52) U.S. Cl.
    CPC ... *A61B 2562/125* (2013.01); *A61B 2562/164*
        (2013.01); *A61N 1/0556* (2013.01)

(56)             References Cited

U.S. PATENT DOCUMENTS

2014/0163348 A1 *   6/2014   Kim .................... A61N 1/0551
                                                  600/377

2016/0331326 A1     11/2016   Xiang et al.
2017/0020403 A1 *   1/2017   Kim .................... A61B 5/6839
2017/0165476 A1     6/2017   Greenberg et al.

FOREIGN PATENT DOCUMENTS

| | | | |
|---|---|---|---|
| CN | 110841186 A | 2/2020 | |
| CN | 111938626 A | 11/2020 | |
| CN | 113015552 A | 6/2021 | |
| CN | 113041496 A | 6/2021 | |
| JP | 2009-285154 A | 12/2009 | |
| KR | 102241887 B1 * | 4/2021 | ......... A61N 1/36135 |
| WO | 2010/060011 A2 | 5/2010 | |
| WO | 2012/139124 A1 | 10/2012 | |
| WO | 2021/141163 A1 | 7/2021 | |

OTHER PUBLICATIONS

Office Action from Chinese Patent Application No. 202210689969.9 dated Jul. 15, 2024.

International Search Report and Written Opinion from International Application No. PCT/CN2022/102335 mailed Dec. 21, 2022.

* cited by examiner

213

214

313

314

613

614

1020

1010

1000

1120

1110

1100

FLEXIBLE ELECTRODE FOR PERIPHERAL NERVE AND METHOD FOR MANUFACTURING SAME

CROSS-REFERENCE TO RELATED APPLICATIONS

This application is a national stage of International Application No. PCT/CN2022/102335 filed on Jun. 29, 2022 which is based on and claims priority to the Chinese application No. 202210689969.9 filed on Jun. 17, 2022. Both of the aforementioned applications are hereby incorporated herein by reference in their entireties.

TECHNICAL FIELD

The present disclosure relates to the field of life science technology, and more particularly, to a flexible electrode for a peripheral nerve and a method for manufacturing the same.

BACKGROUND

In China, approximately 24 million people are suffering from varying degrees of limb disability caused by physical trauma, neurodegenerative diseases, and amputation, etc. Physical limitations have a huge impact on the daily lives of these disabled people. Neural electrodes can be used to control peripheral nerves of severed limbs.

SUMMARY

A brief overview of the present disclosure is given below in order to provide a basic understanding of some aspects of the present disclosure. However, it should be understood that this overview is not an exhaustive overview of the present disclosure. It is not intended to identify the key or important parts of the present disclosure, nor is it intended to limit the scope of the present disclosure. Its purpose is simply to give some concepts of the present disclosure in a simplified form as a prelude to a more detailed description given later.

According to a first aspect of the present disclosure, a flexible electrode for a peripheral nerve is provided. The flexible electrode includes an implantation portion that is capable of being implanted into a truncated peripheral nerve or a nerve stump and is configured to acquire or apply an electrical signal inside and on a surface of a peripheral nerve bundle, wherein: the flexible electrode includes a first insulating layer, a second insulating layer, and a wire layer located between the first insulating layer and the second insulating layer; the implantation portion includes one or more electrode sites, each of which is electrically coupled to one of wires in the wire layer and is in contact with the peripheral nerve after implantation of the flexible electrode to acquire an electrical signal from the peripheral nerve and transmit the acquired electrical signal via the wire, or to apply an electrical signal received via the wire to the peripheral nerve; and the implantation portion has pores to facilitate reconstruction of the peripheral nerve and to be in close contact with the peripheral nerve after the reconstruction.

According to a second aspect of the present disclosure, a method for manufacturing a flexible electrode for a peripheral nerve according to the first aspect of the present disclosure is provided. The method includes: forming the first insulating layer, the wire layer, the second insulating layer, and the electrode site over a substrate; and separating the flexible electrode from the substrate, wherein a through hole is formed at a position corresponding to the electrode site in at least one of the first insulating layer or the second insulating layer by patterning.

Other features of the present disclosure and advantages thereof will become more apparent from the following detailed description of exemplary embodiments of the present disclosure with reference to the accompanying drawings.

BRIEF DESCRIPTION OF THE DRAWINGS

The accompanying drawings, which constitute a part of the specification, illustrate embodiments of the present disclosure and, together with the description, serve to explain the principles of the present disclosure.

The present disclosure can be more clearly understood from the following detailed description with reference to the accompanying drawings, in which.

DETAILED DESCRIPTION

Figure 1:
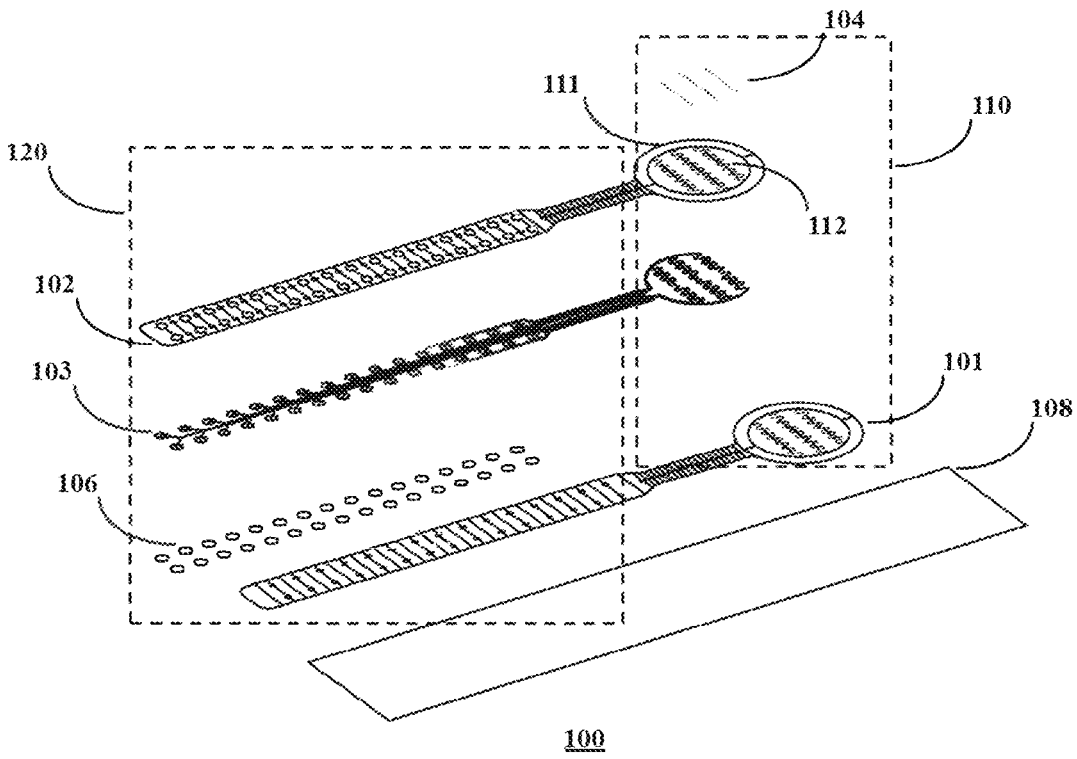
FIG. 1 shows an exploded view of at least a portion of a flexible electrode for a peripheral nerve according to an embodiment of the present disclosure.

The following detailed description is made with reference to the accompanying drawings, and is provided to assist in a comprehensive understanding of various exemplary embodiments of the present disclosure. The following description includes various details to assist in understanding, but these details are considered to be examples only and not to limit the present disclosure, and the present disclosure is defined by the appended claims and their equivalents. The words and phrases used in the following description are only used to enable a clear and consistent understanding of the present disclosure. In addition, for clarity and brevity, descriptions of well-known structures, functions, and configurations may be omitted. Those of ordinary skill in the art will recognize that various changes and modifications may be made to the examples described herein without departing from the spirit and scope of the present disclosure.

The following description of at least one exemplary embodiment is in fact merely illustrative and is in no way intended to limit the present disclosure and its application or use. That is, structures and methods herein are shown in an exemplary manner to illustrate different embodiments of the structures and methods in the present disclosure. However, those skilled in the art will appreciate that they merely illustrate exemplary ways of the present disclosure that can be implemented, rather than exhaustive ways. In addition, the drawings need not be drawn to scale, and some features may be enlarged to illustrate the details of specific components.

Technologies, methods, and devices known to those of ordinary skills in the relevant field may not be discussed in detail, but where appropriate, such technologies, methods, and devices should be considered as a part of the granted specification.

In all examples shown and discussed herein, any specific values should be interpreted as merely exemplary and not as limiting. Therefore, other examples of exemplary embodiments may have different values.

An extrafascicular neural electrode when applied usually wraps the outside of a peripheral nerve bundle, typically with less than 10 sites, and can only record local field potential signals; and due to the presence of immune scars, long-term stable recording and stimulation are impossible. The extrafascicular neural electrodes include Cuff electrodes, FINE electrodes, and flexible Helical electrodes, etc. During use, the extrafascicular neural electrode is assembled on an inner wall of a silicone hose or a flat conduit, and then the silicone hose or flat conduit is wrapped outside of the nerve bundle. Therefore, during use, the silicone hose of the extrafascicular neural electrode that wraps the outside of the nerve may be relatively displaced from the nerve bundle; during long-term use, the friction between the hard conduit and the nerve bundle will cause damage to the nerve, and a scar formed on the nerve will affect the recording and stimulation of signals; the extrafascicular neural electrode can only record compound action potential signals and perform large-scale nerve stimulation, and the accuracy of recording and stimulation is far from meeting the needs of fine control; and in addition, the resolution recorded by the electrode is also low.

An intrafascicular neural electrode usually has its electrode recording end arranged on a long-strip substrate and the substrate is inserted into an electrode in a neural bundle. Common intrafascicular neural electrodes include hard Utah electrodes, Floating electrodes, and Michigan electrodes, etc. The intrafascicular electrode is implanted in a peripheral nerve bundle and can record action potential and local field potential signals at the same time, however, hard electrodes may cause significant damage to tissues, leading to local aggregation of glial cells around the electrodes, and a tip of the hard electrode is relatively brittle and may easily fall off and break, resulting in the inability of long-term stable recording and stimulation.

The bottleneck of the current related technology is how to provide long-term stable multi-channel control signals. Specifically, it is necessary to realize the direct control of peripheral nerves of severed limbs with the potential to output high-throughput fine control signals and receive complex sensory signals including temperature, pressure, and pain senses. Therefore, a peripheral neural electrode with high channel count, high selectivity, ultra-flexibility, and the ability of long-term stable recording and stimulation is urgently needed.

FIG. 1 shows an exploded view of at least a portion of a flexible electrode 100 for a peripheral nerve according to an embodiment of the present disclosure. Utilizing the property of the peripheral nerve being capable of reconstruction, the flexible electrode 100 can be implanted into two nerve segments that are completely truncated, and achieves signal recording and measurement by utilizing the active formation of a close electrode-tissue interface between the electrode and a nerve and a blood vessel during a repairing process therefor, which has better performance than that of the intrafascicular neural electrode and the extrafascicular neural electrode described above.

As shown in FIG. 1, the flexible electrode 100 may include an implantation portion 110, which may be implanted into a truncated peripheral nerve or a nerve stump and is configured to acquire or apply an electrical signal inside and on a surface of a peripheral nerve bundle. The implantation portion 110 may have pores and be stretchable. The pores and stretchability of the implantation portion 110 may facilitate reconstruction of the peripheral nerve into which it is implanted, and after the reconstruction, the implantation portion 110 is caused to be in close contact with the peripheral nerve. The shape and size of the pore may be designed according to the size of the peripheral nerve, and the porosity of the implantation portion 110 is above 70%. In an embodiment according to the present disclosure, the implantation portion 110 may include an outer annular portion 111 and one or more extension portions 112 extending inwards from the outer annular portion 111. In the embodiment shown in FIG. 1, six extension portions 112 extend inwards symmetrically from the outer annular portion 111 in a serpentine manner and are parallel to each other to form the pores between the outer annular portion 111 and the one or more extension portions 112. However, it should be understood that the shape, number and arrangement of the extension portions are not limited thereto. For example, in a flexible electrode 400 shown in FIG. 4, extension portions 412 extend linearly inwards, and this embodiment will be described in detail below. In an embodiment according to the present disclosure, in the flexible electrode 100, these extension portions 112 may also be asymmetric or non-parallel to each other. After implantation, the outer annular portion 111 may surround the reconstructed peripheral nerve, and the one or more extension portions 112 may extend from the outer annular portion 111 to the inside of the peripheral nerve and deform along with the reconstruction of the peripheral nerve. For example, at this time, the one or more extension portions 112 may be stretched longer due to the reconstruction of the peripheral nerve and thus keep close contact with the peripheral nerve, and the serpentine structure of the extension portions 112 and the flexible material for fabricating the flexible electrode 100 may be favorable to such deformation. Moreover, at this time, the one or more extension portions 112 may conform to the reconstruction of the peripheral nerve to have an arrangement different from the arrangement in which the flexible electrode 100 was initially fabricated. For example, the one or more extension portions 112 may not be in the same plane and may not be parallel to each other, but may extend from the outer annular portion 111 in different directions or angles. For example, the two extension portions 112 shown as being collinear in the same plane in FIG. 1 may form an angle. When the flexible electrode 100 is connected or packaged with a back-end circuit after being manufactured, the one or more extension portions 112 may be immersed in a biocompatible adhesive (such as but not limited to low modulus silicone) so that the one or more extension portions 112 are coated with the biocompatible adhesive for waterproof.

Figure 4:
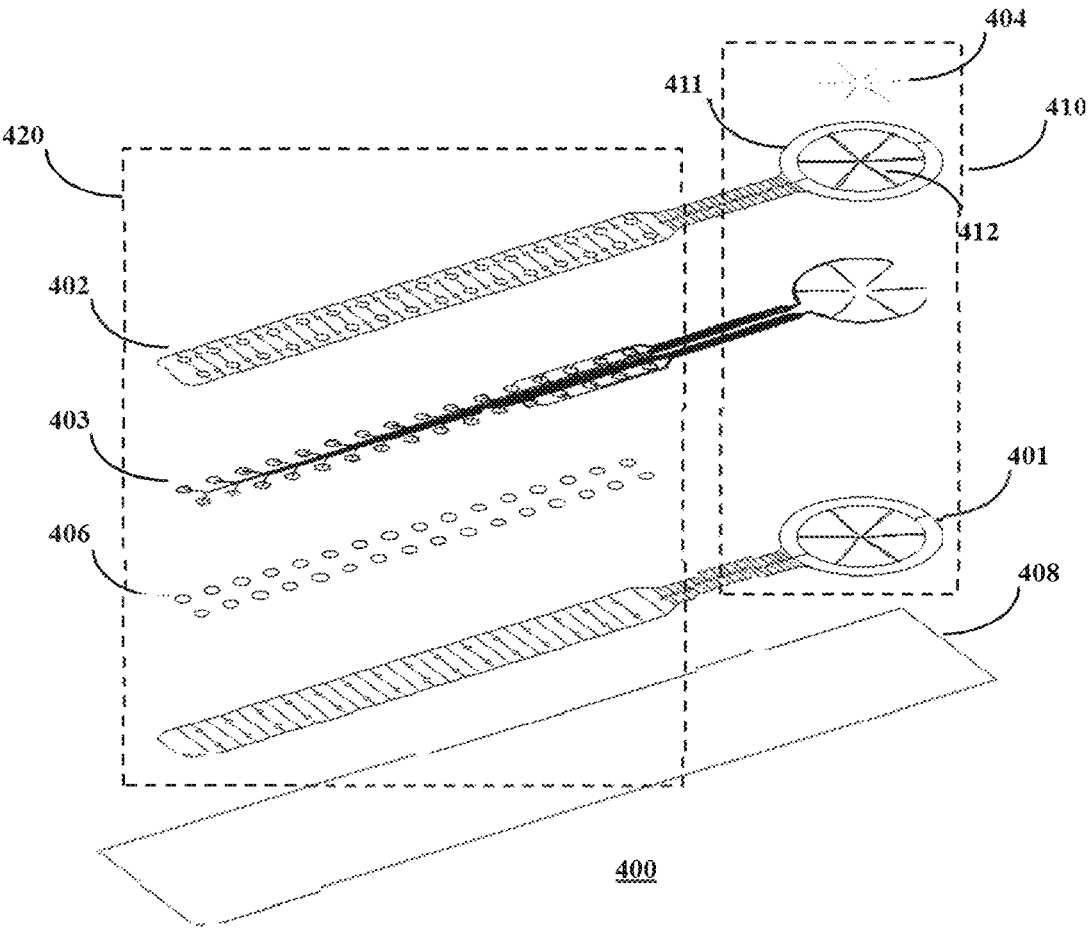
FIG. 4 shows an exploded view of at least a portion of a flexible electrode for a peripheral nerve according to an embodiment of the present disclosure.

In the flexible electrodes shown in FIGS. 1 and 4, the extension portions are shown as linear or serpentine, but it should be understood that the flexible electrode according to the present disclosure is not limited to this, and the extension portions may also take a shape of a horseshoe, wheel, belt, strip, mesh, etc.

In an embodiment according to the present disclosure, the flexible electrode 100 may further include a back-end portion 120, which may be implanted subcutaneously and may be used to engage the flexible electrode 100 and the back-end circuit for back-end adaptation, and the implantation portion 110 extends from the back-end portion 120. The flexible electrode 100 shown in FIG. 1 includes an implantation portion 110 having a circular contour and an elongated back-end portion 120, but it should be understood that FIG. 1 is only a non-limiting example, and the flexible electrode for the peripheral nerve bundle may have an implantation portion 110 and a back-end portion 120 of different shapes and sizes as required.

It can be clearly seen from FIG. 1 that the flexible electrode 100 has a multi-layer structure, specifically including a bottom insulating layer 101, a top insulating layer 102, a wire layer 103, an electrode site layer 104, a back-end site layer 106, and a flexible separation layer 108, etc. It should be understood that the layers of the flexible electrode 100 shown in FIG. 1 are only non-limiting examples, and the flexible electrode in the present disclosure may not include one or more of these layers, or may include more other layers.

The flexible electrode 100 may include an insulating layer 101 at the bottom and an insulating layer 102 at the top. Specifically, as shown in FIG. 1, the implantation portion 110 and the back-end portion 120 of the flexible electrode 100 may each include the insulating layers 101 and 102. An insulating layer in the flexible electrode may refer to an outer surface layer in the electrode that plays an insulating role. Since the insulating layer of the flexible electrode needs to be in contact with a biological tissue after implantation, a material of the insulating layer is required to have good biocompatibility while having good insulation property. In an embodiment of the present disclosure, the material of the insulating layers 101 and 102 may include polyimide (PI), polydimethylsiloxane (PDMS), Parylene, epoxy resin, polyamide imide (PAI), SU-8 photoresist, silica gel, silicone rubber, etc. In an embodiment according to the present disclosure, in order to make the flexible electrode further have biodegradability, the material of the insulating layers 101 and 102 may also include polylactic acid, polylactic acid—glycolic acid copolymer, etc. In addition, the insulating layers 101 and 102 are also main parts that provide strength in the flexible electrode 100. If the insulating layer is too thin, the strength of the electrode will be reduced; and if the insulating layer is too thick, the flexibility of the electrode will be reduced. In addition, the implantation of an electrode including an overly thick insulating layer will cause greater damage to the organism. In an embodiment according to the present disclosure, the thickness of the insulating layers 101 and 102 may be 100 nm to 300 μm.

In an embodiment according to the present disclosure, the outer annular portion 111 of the flexible electrode 100 may be thickened as compared to other portions (such as the extension portion 112, etc.) to provide higher strength. For example, at least one of the bottom insulating layer 101 or the top insulating layer 102 at the outer annular portion 111 may be thickened.

The flexible electrode 100 may further include wires in the wire layer 103 between the bottom insulating layer 101 and the top insulating layer 102. Specifically, as shown in FIG. 1, the implantation portion 110 and the back-end portion 120 of the flexible electrode 100 may each include the wire layer 103. In an embodiment according to the present disclosure, these wires extend along the back-end portion 120 to the implantation portion 110, and extend in the implantation portion 110 along at least a portion of the outer annular portion 111 and one of the extension portions 112 to an electrode site located on the extension portion 112. In an embodiment according to the present disclosure, the flexible electrode 100 may include one or more wires in the same wire layer 103, wherein each wire may be electrically coupled to an electrode site in the electrode site layer 104 and electrically coupled to a back-end site in the back-end site layer 106. Each wire may have a micrometer-level width and a nanometer-level thickness. In an embodiment of the present disclosure, the thickness of the wire layer 103 and each wire therein may be 5 nm to 200 μm. The spacing between the wires may be as low as 10 nm, for example. The line width of the wire and the spacing between the wires may be, for example, 10 nm to 500 μm, for example, preferably 100 nm to 30 μm. It should be understood that the size of the wire is not limited to the above-listed ranges, but may vary according to design requirements.

In an embodiment according to the present disclosure, the wire in the wire layer 103 may have a thin film structure including multiple sub-layers stacked in the thickness direction. The materials of these sub-layers may be materials that can enhance the adhesion, ductility, conductivity, etc., of the wires. As a non-limiting example, the wire layer 103 may be a metal film including three sub-layers stacked, wherein a first sub-layer and a second sub-layer that are in contact with the insulating layers 101 and 102 respectively, are adhesion sub-layers, and may adopt metal adhesive materials such as titanium (Ti), titanium nitride (TiN), chromium (Cr), tantalum (Ta) or tantalum nitride (TaN) or non-metal adhesive materials; and a third sub-layer located between the first sub-layer and the second sub-layer is a conductive sub-layer, and may adopt materials with good conductivity such as gold (Au), platinum (Pt), iridium (Ir), tungsten (W), platinum-iridium alloy, titanium alloy, graphite, carbon nanotubes, PEDOT, etc. In an embodiment according to the present disclosure, in order to make the flexible electrode further have biodegradability, the conductive sub-layer may also adopt materials such as magnesium (Mg), molybdenum (Mo) and alloys thereof. It should be understood that the wire layer may be made of other metal or non-metal materials that have conductivity, or may be made of polymeric conductive materials and composite conductive materials. In an embodiment according to the present disclosure, the thickness of the adhesion sub-layer may be 1 nm to 50 nm.

The flexible electrode 100 may also include electrode sites in the top electrode site layer 104 located above the top insulating layer 102, and each of the electrode sites is electrically coupled to one of the wires in the wire layer 103 and is in contact with the peripheral nerve after the flexible electrode 100 is implanted, to acquire electrical signals from the peripheral nerve and transmit the acquired electrical signals through the wires, or to apply electrical signals received through the wires to the peripheral nerve.

In the flexible electrode 100 shown in FIG. 1, each of the six extension portions 112 in the implantation portion 110 includes a plurality of corresponding electrode sites, wherein the electrode sites closer to the outer annular portion 111 may be used to apply or acquire signals at the surface of the peripheral nerve, and the electrode sites farther from the outer annular portion 111 may be used to apply or acquire signals inside the peripheral nerve. However, it should be understood that the present disclosure is not limited thereto, and each extension portion of the flexible electrode may include one or more electrode sites for applying or acquiring a signal inside and on the surface of the peripheral nerve as needed. In addition, since each electrode site is coupled to its corresponding wire, when the flexible electrode 100 is used as a stimulation electrode, each of the electrode sites can synchronously or asynchronously apply the same or different electrical signals at a deep part of and/or at different locations of the surface of the peripheral nerve; and when the flexible electrode 100 is used as a recording electrode, these electrode sites can simultaneously and finely acquire electrical signals at a deep part of and/or at different locations of the surface of the peripheral nerve.

Figure 2:
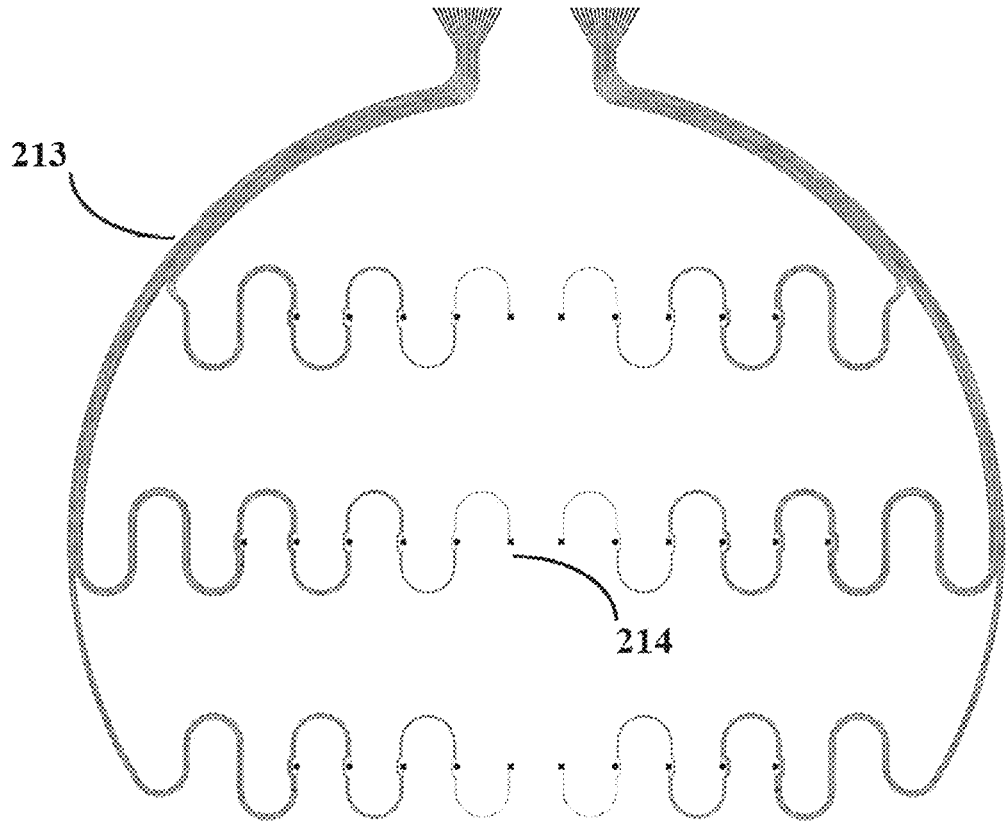
FIG. 2 shows an enlarged view of at least a portion of wires and electrode sites at an implantation portion of a flexible electrode for a peripheral nerve according to an embodiment of the present disclosure.

FIG. 2 shows an enlarged view of at least a portion of wires and electrode sites at an implantation portion of a flexible electrode for a peripheral nerve according to an embodiment of the present disclosure, which is an enlarged view of at least a portion of the wires and the electrode sites of the implantation portion 110 as shown in FIG. 1. As shown in FIG. 2, a wire 213 extends along at least a portion of the outer annular portion of the implantation portion, then extends in a serpentine manner along the extension portion of the implantation portion, and is electrically coupled to a corresponding electrode site 214. Here, the wire 213 and the electrode site 214 may be located in different layers, for example, the wire 213 is located in the wire layer 103 as shown in FIG. 1, and the electrode site 214 is located in the top electrode site layer 104 as shown in FIG. 1; or the wire 213 and the electrode site 214 may also be located in the same layer, that is, the flexible electrode may not include an electrode site layer, the wire and the electrode site are both located in the wire layer between the top insulating layer and the bottom insulating layer, and the electrode site 214 is exposed at the outer surface of the electrode via a through hole in at least one of the top insulating layer or the bottom insulating layer and contacts the peripheral nerve.

Figure 3:
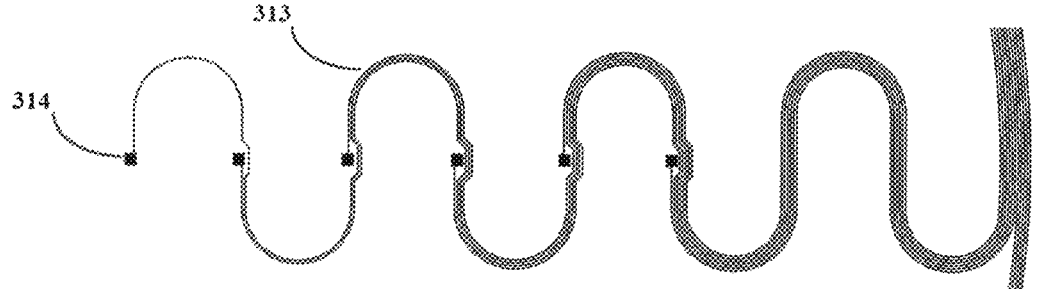
FIG. 3 shows an enlarged view of at least a portion of wires and electrode sites of an extension portion at an implantation portion of a flexible electrode for a peripheral nerve according to an embodiment of the present disclosure.

FIG. 3 shows an enlarged view of at least a portion of wires and electrode sites of one extension portion at an implantation portion of a flexible electrode for a peripheral nerve according to an embodiment of the present disclosure, which is an enlarged view of at least a portion of the wires and the electrode sites in one of the six extension portions 112 shown in FIG. 1. As shown in FIG. 3, each extension portion may include a plurality of wires 313 extending in a serpentine manner along the extension portion and a corresponding plurality of electrode sites 314, wherein each electrode site 314 is coupled to a corresponding one of the wires 313, and the wires 313 are spaced apart from each other by a distance and extend in a serpentine manner in parallel to each other.

Referring back to FIG. 1, in the flexible electrode 100, the electrode sites in the top electrode site layer 104 can be electrically coupled to the corresponding wires via the through holes in the top insulating layer 102 at the positions corresponding to the electrode sites. In the case where the flexible electrode includes a plurality of wires, the flexible electrode may correspondingly include a plurality of electrode sites in the top electrode site layer 104, and each of these electrode sites is electrically coupled to one of the plurality of wires via a corresponding through hole in the top insulating layer 102. In an embodiment according to the present disclosure, the electrode sites in the top electrode site layer 104 may have a thin film structure including a plurality of sub-layers stacked in the thickness direction. The material of the adhesion sub-layer close to the wire layer 103 among the plurality of sub-layers may be a material that can enhance the adhesion between the electrode sites and the wires, and the thickness of the adhesion sub-layer may be 1 nm to 50 nm. As a non-limiting example, the electrode site layer 104 may be a metal film including two superimposed sub-layers, wherein a first sub-layer close to the wire layer 103 is Ti, TiN, Cr, Ta or TaN, and a second sub-layer of the electrode site layer 104 that is exposed to the outside is Au. It should be understood that the electrode site layer may also be similar to the wire layer and may be made of other metal or non-metal materials that have conductivity, such as Pt, Ir, W, Mg, Mo, platinum-iridium alloy, titanium alloy, graphite, carbon nanotubes, PEDOT, etc.

Each electrode site may have a planar size at the micrometer level and a thickness at the nanometer level. In the embodiments according to the present disclosure, the electrode site may be shaped to have various regular or irregular shapes as required, a number of the electrode sites may be one or more, a maximum side length or diameter of the electrode site may be 1 μm to 500 μm, a spacing between the electrode sites may be 10 μm to 10 mm, and a thickness of the electrode site may be 5 nm to 200 μm. It should be understood that the shape, number, size and spacing of the electrode sites may be selected according to the situation of the biological tissue area required to be recorded or stimulated.

In an embodiment according to the present disclosure, the surface of the electrode site that is exposed to the outside and in contact with the biological tissue may also have a surface modification layer to improve the electrochemical properties of the electrode site. As a non-limiting example, the surface modification layer may be obtained by using an electro-induced polymerization coating of PEDOT:PSS, sputtering an iridium oxide film, and the like, for reducing impedance (such as electrochemical impedance at an operating frequency of 1 kHz) in a case where the flexible electrode acquires electrical signals, and for improving charge injection capability in a case where the flexible electrode applies electrical signals for stimulation, thereby improving interaction efficiency.

In an embodiment according to the present disclosure, although not shown in FIG. 1, the flexible electrode may further include an electrode site in a bottom electrode site layer 105 located below the bottom insulating layer 101, and the electrode site may contact a biological tissue after the flexible electrode is implanted to directly acquire or apply an electrical signal. Similar to the electrode sites in the top electrode site layer 104, in the flexible electrode 100, electrode sites in the bottom electrode site layer 105 may be electrically coupled to corresponding wires via through holes in the bottom insulating layer 101 at positions corresponding to the electrode sites. In an embodiment according to the present disclosure, the electrode site in the bottom electrode site layer 105 and the electrode site in the top electrode site layer 104 may be located at opposite positions on the bottom and top sides of the flexible electrode 100, and may be electrically coupled to the same wire in the wire layer 103. In an embodiment according to the present disclosure, the electrode site in the bottom electrode site layer 105 and the electrode site in the top electrode site layer 104 may also be located at different positions on the bottom and top sides of the flexible electrode 100 to acquire or apply an electrical signal in different areas of a biological tissue; and in an embodiment according to the present disclosure, the electrode site in the bottom electrode site layer 105 and the electrode site in the top electrode site layer 104 may also be electrically coupled to different wires in the wire layer 103.

It should be understood that the bottom electrode site layer 105 is an optional part but not a necessary part of the flexible electrode. For example, the flexible electrode in the present disclosure may include only the top electrode site layer 104 without including the bottom electrode site layer 105. The shape, size, material, etc. of the bottom electrode sites may be similar to those of the top electrode sites and will not be described in detail here.

In an embodiment of the present disclosure, the flexible electrode may further include an additional wire layer, that is, the flexible electrode in the present disclosure may include one or more wire layers. The size, material, fabrication method, etc. of the additional wire layer may be similar to those of the wire layer 103, and will not be described in detail here. In the case where the flexible electrode includes an additional wire layer, these wire layers may be separated from each other by an additional insulating layer, and the size, material, and fabrication method of the additional insulating layer may be similar to those of the bottom insulating layer 101 and/or the top insulating layer 102, and will not be described in detail here. One or more wires in these additional wire layers may be electrically coupled to electrode sites located below the bottom insulating layer or above the top insulating layer via through holes in one or more of the bottom insulating layer, the top insulating layer, and the additional insulating layers. By including multiple wire layers in the flexible electrode, the number and accuracy of signals transmitted through the flexible electrode can be increased with the same section width, that is, a high-accuracy and multi-channel electrode is provided, which is conducive to achieving high-throughput interaction.

In an embodiment according to the present disclosure, the back-end portion 120 of the flexible electrode 100 may include a back-end site in the back-end site layer 106, and the back-end site may be electrically coupled to one of the wires (FIG. 1 shows that the back-end site in the back-end site layer 106 is electrically coupled to a metal ring at an end of the one of the wires) and electrically coupled to the back-end circuit via a through hole in at least one of the bottom insulating layer 101 or the top insulating layer 102, so as to achieve bidirectional signal transmission between the electrode site electrically coupled to the wire and the back-end circuit. In an embodiment according to the present disclosure, as shown in FIG. 1, the back-end site is located between the wire layer 103 and the bottom insulating layer 101, and the back-end site can be electrically coupled to the back-end circuit via the metal ring of the wire layer 103 and the through hole in the top insulating layer 102. In this arrangement, the back-end site is not placed on the outer surface of the flexible electrode 100, thereby facilitating a stable connection between the flexible electrode 100 and the back-end circuit. Here, the back-end circuit may refer to a circuit at the back end of the flexible electrode, such as a signal recording circuit, a signal processing circuit, a signal generating circuit, etc., associated with the signal of the flexible electrode. In an embodiment according to the present disclosure, the flexible electrode may be coupled to the back-end circuit in a connection manner. Specifically, the ball grid array (BGA) package sites as back-end sites can be adapted to a commercial signal recording system through a printed circuit board (PCB), a flexible printed circuit (FPC), etc. The connection manner includes solder ball attachment and anisotropic conductive film bonding (ACF Bonding), etc.

The back-end site may have a planar size at the micrometer level and a thickness at the nanometer level. As a non-limiting example, the back-end site may be the BGA package site with a diameter of 50 μm to 2000 μm, or may be a circular, elliptical, rectangular, rounded rectangular, or chamfered rectangular site with a side length of 50 μm to 2000 μm, and the thickness of the back-end site layer 106 and the back-end sites therein may be 5 nm to 200 μm. It should be understood that the shape, size, etc. of the back-end sites are not limited to the ranges listed above, but may vary according to design requirements.

The back-end site in the connection manner may include multiple sub-layers in the thickness direction, a material of an adhesion sub-layer close to the wire layer 103 among the multiple sub-layers may be a material that can enhance the adhesion between the back-end site and the wire; a material of a flux sub-layer in the middle among the multiple sub-layers may be a flux material; a material of a conductive sub-layer among the multiple sub-layers may be other conductive metal or non-metallic material such as that of the wire layer mentioned above; and an outermost layer among the multiple sub-layers that may be exposed through the insulating layers 101 and 102 is an anti-oxidation protective sub-layer. As a non-limiting example, the back-end site layer 106 may be a metal film including three superimposed sub-layers, wherein a first sub-layer close to the wire layer 103 may be an adhesion sub-layer in nanometer-scale to improve the adhesion between the back-end site layer 106 and the wire layer 103. The material of the first sub-layer as the adhesion sub-layer may be Cr, Ta, TaN, Ti or TiN, the material of the second sub-layer as the flux sub-layer may be nickel (Ni), Pt or palladium (Pd), and the material of the third sub-layer as the conductive sub-layer may be Au, Pt, Ir, W, Mg, Mo, platinum-iridium alloy, titanium alloy, graphite, carbon nanotubes, PEDOT, etc. It should be understood that the back-end site layer may also be made of other metal or non-metallic materials that have conductivity. The back-end site layer 106 in FIG. 1 serves as a part connected to a back-end processing system or chip, and the design of the size, spacing, shape, etc., of sites therein may be changed according to different connection manners at the back end.

In an embodiment according to the present disclosure, the flexible electrode 100 and the back-end circuit connected to the back-end portion 120 may be packaged together by any one of epoxy resin or polydimethylsiloxane or a combination thereof to improve their strength.

In an embodiment according to the present disclosure, the flexible electrode may not include the site layers such as the top electrode site layer, the bottom electrode site layer, and the back-end site layer, etc. In this case, the electrode sites on the electrode and the back-end sites in the back-end portion for adaptation may both be parts of the wire layer, and electrically coupled to corresponding wires in the wire layer. Furthermore, the electrode sites for sensing and applying electrical signals may directly contact the tissue area into which the electrode is implanted. As a non-limiting example, each electrode site may be electrically coupled in the wire layer to a corresponding wire in the wire layer, and exposed at the outer surface of the electrode via corresponding through holes in the top insulating layer or the bottom insulating layer and in contact with a biological tissue.

In an embodiment according to the present disclosure, the flexible electrode 100 may further include the flexible separation layer 108. The flexible separation layer 108 of the flexible electrode 100 in FIG. 1 is shown as the lowest layer of the entire flexible electrode, but it should be understood that the position of the flexible separation layer is not limited thereto, and the flexible electrode may include therein one or more flexible separation layers located at different positions. Preferably, the flexible separation layer may be formed between the substrate and the bottom insulating layer. The flexible separation layer may be made of a material that can be removed by a specific substance (such as a solution) to separate two parts of the flexible electrode above and below the flexible separation layer while avoiding damage to the flexible electrode. Specifically, the flexible separation layer may be used to separate the entire electrode or only the flexible part of the electrode from the substrate, to separate the flexible substrate from a hard substrate, to separate a part that has too strong adhesion and needs to be separated, etc. In an embodiment of the present disclosure, the material of the flexible separation layer may be a metal such as Ni, Cr, aluminum (Al), etc., or non-metal material.

FIG. 4 shows an exploded view of at least a portion of a flexible electrode 400 for a peripheral nerve according to an embodiment of the present disclosure. The flexible electrode 400 is similar to the flexible electrode 100 described above with reference to FIG. 1, which can be implanted into two nerve segments that are completely truncated, and achieves signal recording and measurement by utilizing the active formation of a close electrode-tissue interface between the electrode and a nerve and a blood vessel during a repairing process therefor.

As shown in FIG. 4, the flexible electrode 400 may include an implantation portion 410, which may be implanted into a truncated peripheral nerve or a nerve stump and is configured to acquire or apply an electrical signal inside and on a surface of a peripheral nerve bundle. The implantation portion 410 may have pores and be stretchable, and the pores and stretchability of the implantation portion 410 may facilitate the reconstruction of the peripheral nerve into which it is implanted, and after reconstruction, the implantation portion 410 may be in close contact with the peripheral nerve. The shape and size of the pores may be designed according to the size of the peripheral nerve, and the porosity of the implantation portion 410 may be above 70%. In an embodiment according to the present disclosure, the implantation portion 410 may include an outer annular portion 411 and one or more extension portions 412 extending inwards from the outer annular portion 411. In the embodiment shown in FIG. 4, six extension portions 412 linearly extend inwards radially from the outer annular portion 411 in a symmetrical manner, respectively, to form fan-shaped pores between the outer annular portion 411 and the extension portions 412. However, it should be understood that the shape, number, and arrangement of the extension portions are not limited thereto. In the flexible electrode 400, the extension portions 412 may also be asymmetric to each other. After implantation, the outer annular portion 411 may surround the reconstructed peripheral nerve, and the one or more extension portions 412 may extend inside the peripheral nerve and deform along with the reconstruction of the peripheral nerve. For example, at this time, the one or more extension portions 412 may be stretched longer due to the reconstruction of the peripheral nerve and thus keep close contact with the peripheral nerve, and the flexible material for fabricating the flexible electrode 400 may facilitate such deformation. Moreover, at this time, the one or more extension portions 412 may conform to the reconstruction of the peripheral nerve to have an arrangement different from the arrangement in which the flexible electrode 400 was initially fabricated. For example, the one or more extension portions 412 may not be in the same plane and may be asymmetric to each other, but may instead extend from the outer annular portion 411 in different directions or angles. For example, the two extension portions 412 shown as being collinear in the same plane in FIG. 4 may form an angle. After the flexible electrode 400 is fabricated, the one or more extension portions 412 may be immersed in a biocompatible adhesive (such as but not limited to low modulus silicone) so that the one or more extension portions 412 are coated with the biocompatible adhesive for waterproof.

In an embodiment according to the present disclosure, the flexible electrode 400 may further include a back-end portion 420, which may be implanted subcutaneously and may be used to engage the flexible electrode 400 and a back-end circuit for back-end adaptation, and the implantation portion 410 extends from the back-end portion 420. The flexible electrode 400 shown in FIG. 4 includes an implantation portion 410 having a circular contour and an elongated back-end portion 420, but it should be understood that FIG. 4 is only a non-limiting example, and the flexible electrode for the peripheral nerve bundle may have an implantation portion 410 and a back-end portion 420 of different shapes and sizes as required.

Similar to the flexible electrode 100 shown in FIG. 1, it can be clearly seen that the flexible electrode 400 has a multi-layer structure, specifically including a bottom insulating layer 401, a top insulating layer 402, a wire layer 403, an electrode site layer 404, a back-end site layer 406, and a flexible separation layer 408, etc. These layers are similar to the bottom insulating layer 101, the top insulating layer 102, the wire layer 103, the electrode site layer 104, the back-end site layer 106, and the flexible separation layer 108 described above with respect to the flexible electrode 100 of FIG. 1, and are not described in detail here. It should be understood that the layers of the flexible electrode 400 shown in FIG. 4 are only non-limiting examples, and the flexible electrode in the present disclosure may not include one or more of these layers, or may include more other layers.

Figure 5:
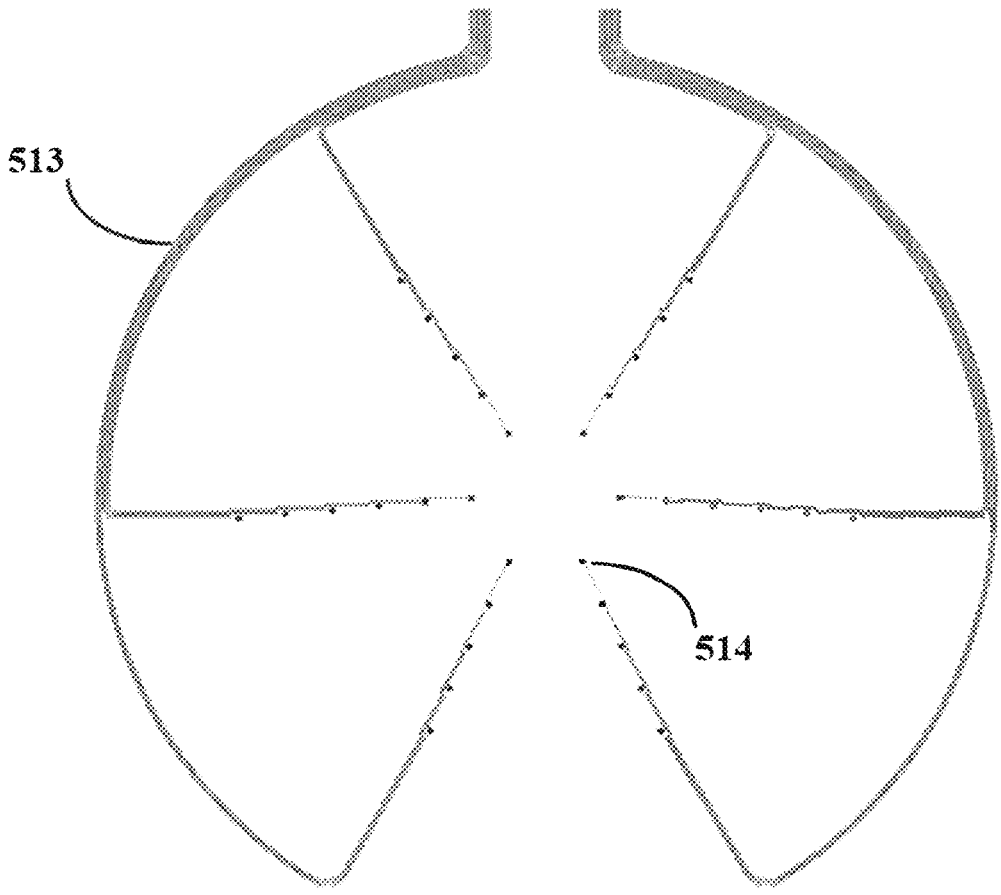
FIG. 5 shows an enlarged view of at least a portion of wires and electrode sites at an implantation portion of a flexible electrode for a peripheral nerve according to an embodiment of the present disclosure.

FIG. 5 shows an enlarged view of at least a portion of wires and electrode sites at an implantation portion of a flexible electrode for a peripheral nerve according to an embodiment of the present disclosure, which is an enlarged view of at least a portion of the wires and electrode sites of the implantation portion 410 as shown in FIG. 4. As shown in FIG. 5, a wire 513 extends along at least a portion of the outer annular portion of the implantation portion, then extends linearly along the extension portion of the implantation portion, and is electrically coupled to a corresponding electrode site 514. Here, the wire 513 and the electrode site 514 may be located in different layers, for example, the wire 513 is located in the wire layer 403 as shown in FIG. 4, and the electrode site 514 is located in the top electrode site layer 404 as shown in FIG. 4; or the wire 513 and the electrode site 514 may also be located in the same layer, that is, the flexible electrode may not include an electrode site layer, the wire and the electrode site are both located in the wire layer between the top insulating layer and the bottom insulating layer, and the electrode site 514 is exposed at the outer surface of the electrode via a through hole in at least one of the top insulating layer or the bottom insulating layer and contacts the peripheral nerve.

Figure 6:
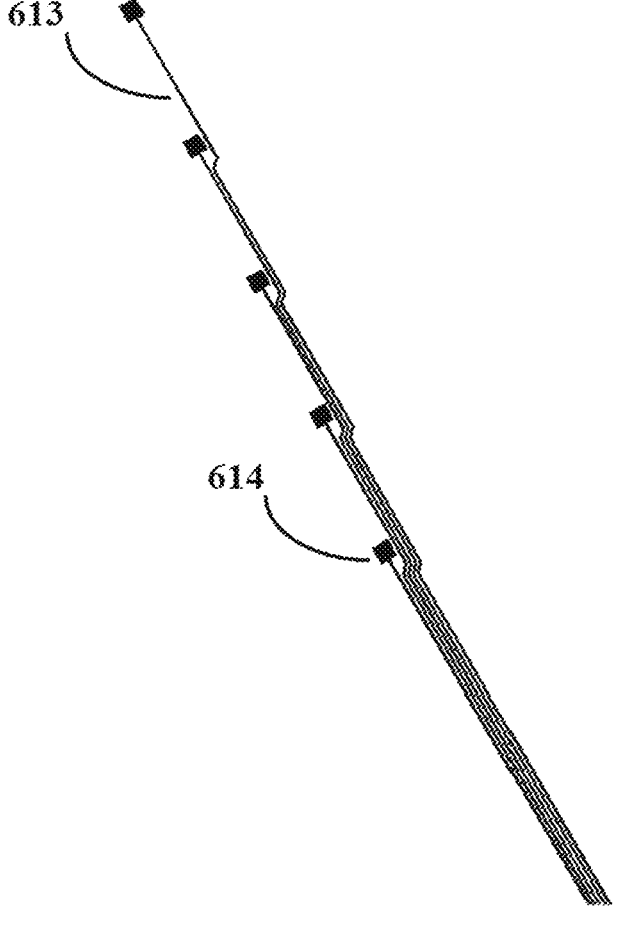
FIG. 6 shows an enlarged view of at least a portion of wires and electrode sites of an extension portion of an implantation portion of a flexible electrode for a peripheral nerve according to an embodiment of the present disclosure.

FIG. 6 shows an enlarged view of at least a portion of wires and electrode sites of an extension portion of an implantation portion of a flexible electrode for a peripheral nerve according to an embodiment of the present disclosure, which is an enlarged view of at least a portion of the wires and electrode sites in one of the six extension portions 412 as shown in FIG. 4. As shown in FIG. 6, each extension portion may include a plurality of wires 613 extending linearly along the extension portion and a corresponding plurality of electrode sites 614, wherein each electrode site 614 is coupled to a corresponding one of the wires 613, and the wires 613 are spaced apart from each other by a distance and extend linearly in parallel to each other.

Figure 7:
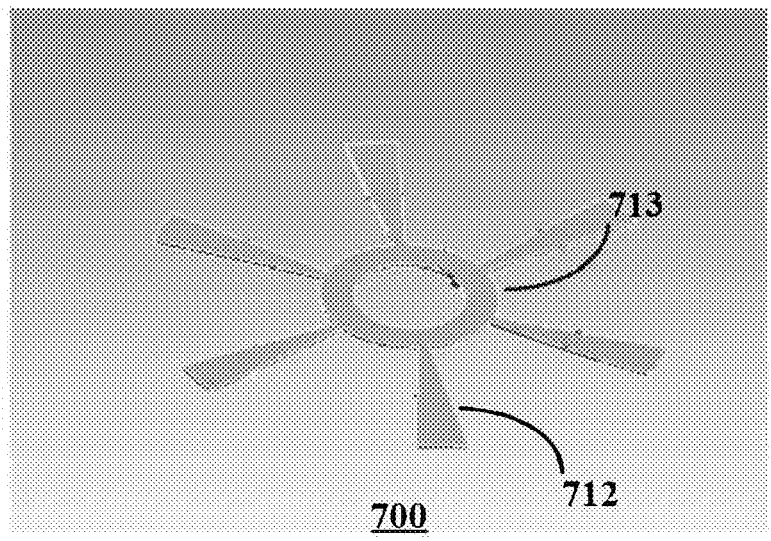
FIG. 7 shows an enlarged view of an extension portion and an inner annular portion of an implantation portion of a flexible electrode for a peripheral nerve according to an embodiment of the present disclosure.

FIG. 7 shows an enlarged view of extension portions and an inner annular portion of an implantation portion of a flexible electrode for a peripheral nerve according to an embodiment of the present disclosure, which shows at least a portion of a preferred embodiment of the flexible electrode 400 shown in FIG. 4, and the implantation portion shown in FIG. 7 includes an inner annular portion 713 in addition to an outer annular portion and one or more extension portions extending inwards from the outer annular portion, respectively. As shown in FIG. 7, one or more extension portions 712 extend radially from the outer annular portion (not shown in FIG. 7) to the inner annular portion 713, respectively, being narrowed at a position where they meet the inner annular portion 713, and may be deformed or disconnected from the inner annular portion 713 during the reconstruction of the peripheral nerve after implantation. The structure having such an inner annular portion can further provide a space for the reconstruction of the peripheral nerve. In an embodiment according to the present disclosure, the inner annular portion 713 may be provided with a wire and an electrode site, for example, the wire may extend along the back-end portion, at least a portion of the outer annular portion, and the extension portion to the inner annular portion 713 and be electrically coupled to the electrode site at the inner annular portion 713. In an embodiment according to the present disclosure, the inner annular portion 713 may not be provided with a wire and an electrode site, and may only include at least one of the top insulating layer or the bottom insulating layer. As a non-limiting example, in the structure shown in FIG. 7, the inner annular portion 713 may have an outer diameter of 300 nm to 10 μm, an inner diameter of 250 nm to 40 μm, and a width of 5 μm to 40 μm.

Figure 12:
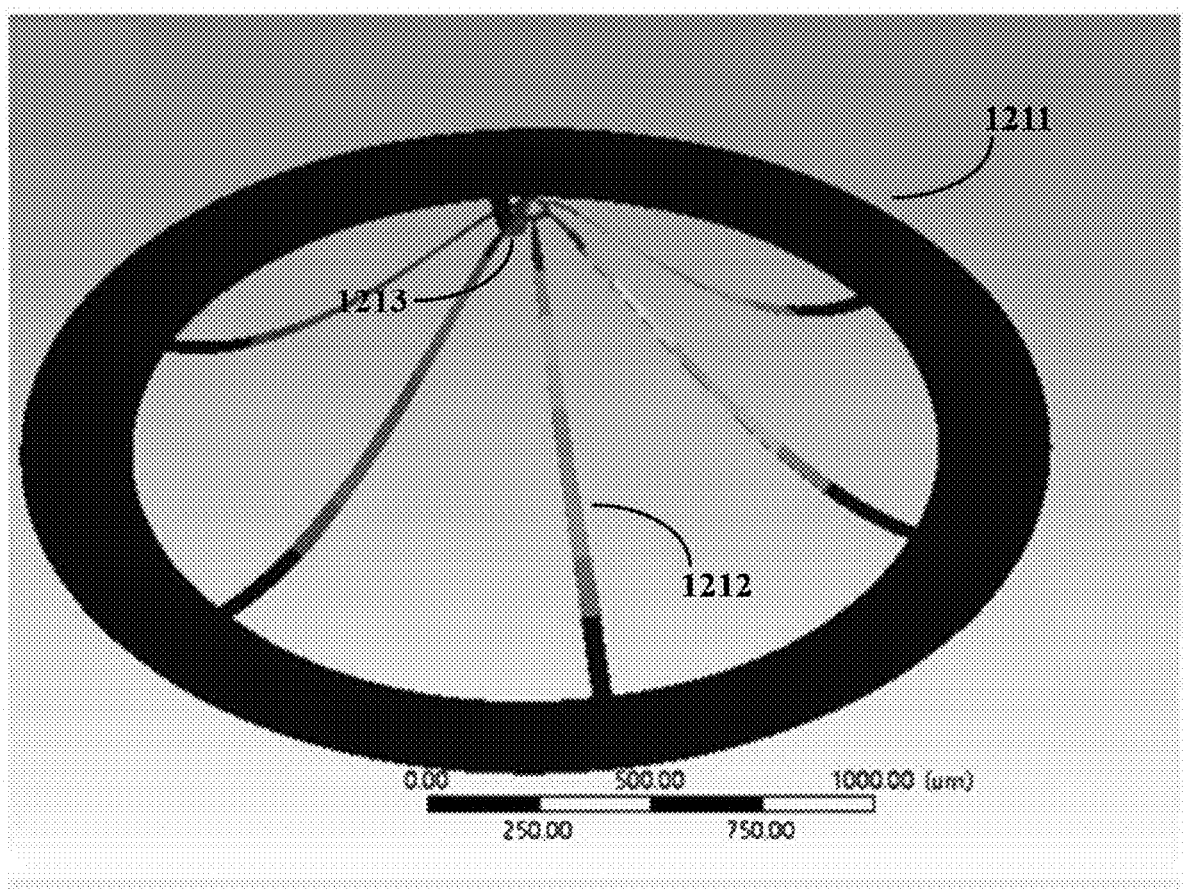
FIG. 12 shows a schematic diagram of an implantation portion of a flexible electrode that is deformed according to an embodiment of the present disclosure.

FIG. 12 is a schematic diagram showing the deformation of the implantation portion of the flexible electrode according to an embodiment of the present disclosure. As shown in FIG. 12, during the reconstruction of the peripheral nerve after the flexible electrode is implanted, the implantation portion of the flexible electrode will deform, wherein an extension portion 1212 extending from an outer annular portion 1211 will deform along with the reconstruction, such as being stretched; and an inner annular portion 1213 to which the extension portion 1212 extends will shift along with the reconstruction, such as no longer being in the same plane as the rest of the implantation portion. In addition, when the stress applied to the implantation portion due to the reconstruction of the peripheral nerve reaches a certain value, the inner annular portion 1213 will be disconnected from the flexible electrode, so as to separate from the extension portion 1212.

In an embodiment according to the present disclosure, the internal portion of the implantation portion of the flexible electrode (such as but not limited to the extension portion and/or the inner annular portion described above) may be configured to be deformed or at least partially disconnected from the implantation portion during the reconstruction of the peripheral nerve after implantation.

In an embodiment according to the present disclosure, after the flexible electrode is fabricated, the flexible electrode can be separated from the substrate on which it is fabricated (such as, being separated from the substrate by removing its flexible separation layer), and then the flexible electrode can be connected (for example, welded) to the back-end circuit. In an embodiment according to the present disclosure, the flexible electrode and the back-end circuit connected to the back-end portion may be packaged together by any one of epoxy resin or polydimethylsiloxane or a combination thereof to improve their strength. In an embodiment according to the present disclosure, a gap in the package of the back-end portion and the back-end circuit is coated with a high-viscosity waterproof glue to ensure the waterproofness of the connection between the flexible electrode and the back-end circuit after implantation.

Figure 10:
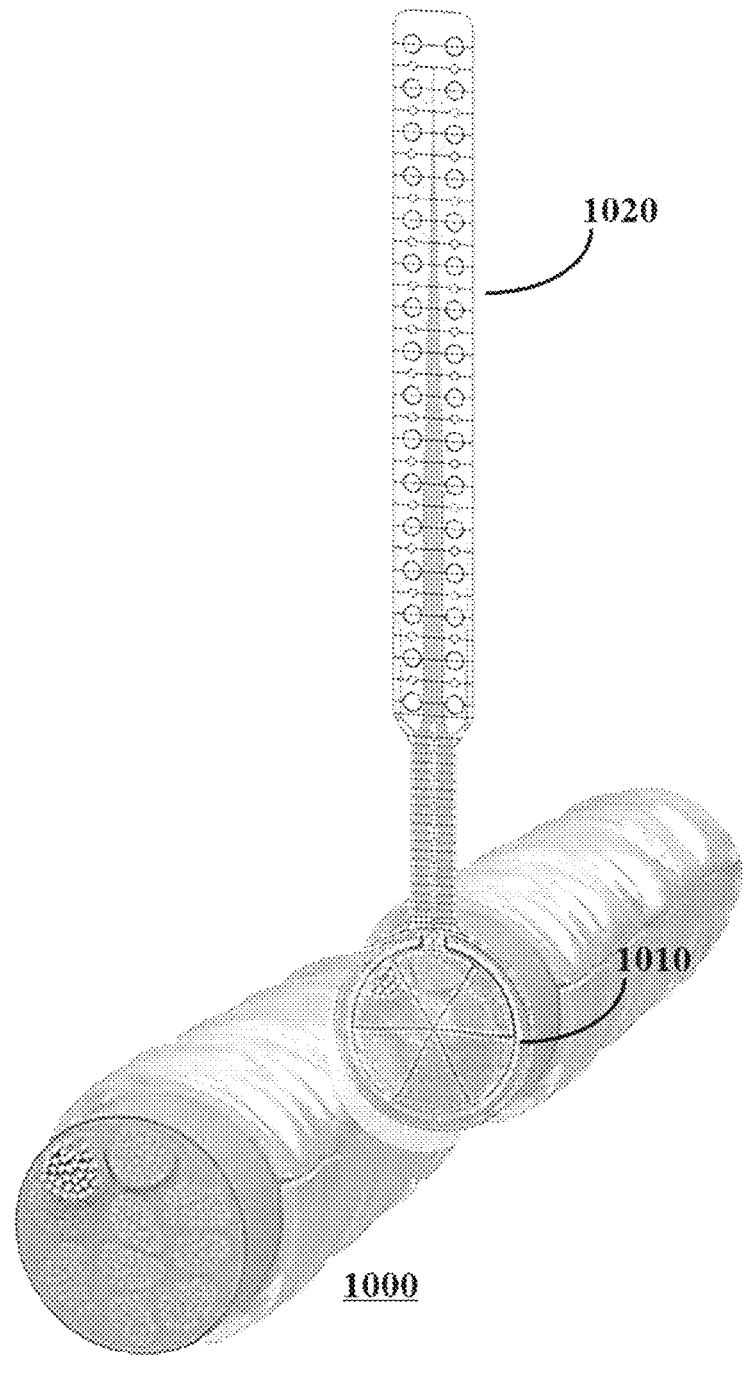
FIG. 10 shows a schematic diagram of an implantation method of a flexible electrode for a peripheral nerve according to an embodiment of the present disclosure.
Figure 11:
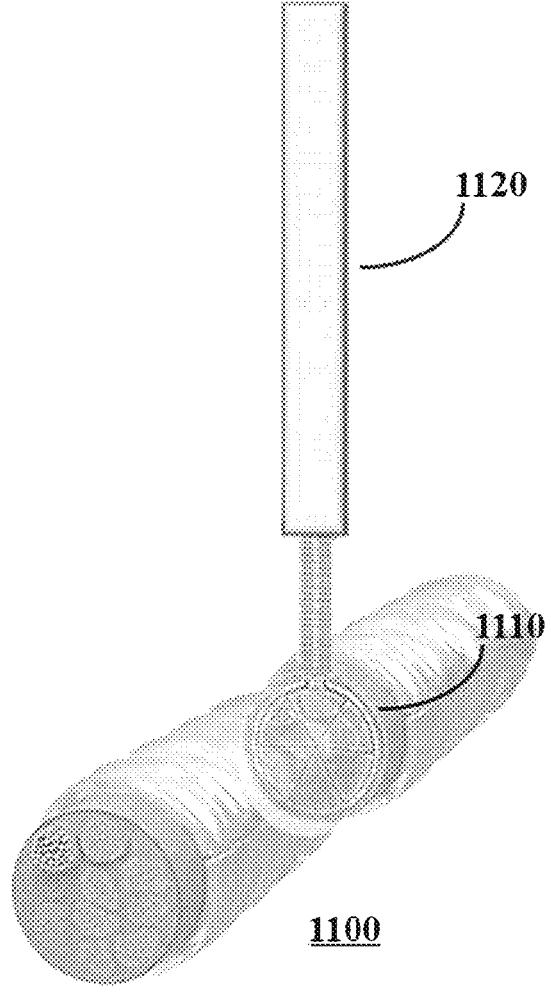
FIG. 11 shows a schematic diagram of an implantation method of a flexible electrode for a peripheral nerve according to an embodiment of the present disclosure.

FIG. 10 shows a schematic diagram of an implantation method of a flexible electrode 1000 for a peripheral nerve according to an embodiment of the present disclosure. As shown in FIG. 10, an implantation portion 1010 of the flexible electrode 1000 can be placed between truncated peripheral nerves or at a nerve stump, and a back-end portion 1020 is placed outside the peripheral nerve and can be implanted subcutaneously. FIG. 11 shows a schematic diagram of an implantation method of a flexible electrode 1100 for a peripheral nerve according to an embodiment of the present disclosure. As shown in FIG. 11, an implantation portion 1110 of the flexible electrode 1100 can be placed between truncated peripheral nerves or at a nerve stump, and a back-end portion 1120 can be packaged together with a back-end circuit before implantation, and placed outside the peripheral nerve and implanted subcutaneously during implantation. During implantation, a neck of the flexible electrode between the implantation portion and the back-end portion may also be coated with a biocompatible adhesive (such as but not limited to silica gel). The neck is also located inside the body after the flexible electrode is implanted, so its biocompatibility needs to be improved.

In an embodiment according to the present disclosure, the implantation of the flexible electrode may include the following steps: the truncated peripheral nerves are respectively inserted into a conduit kit for assisting implantation, and the conduit kit is fixed to the peripheral nerves by using a neural surgical suture; the flexible electrode is laid flat between cross-sections of two segments of the conduit kit, and the electrode sites of the implantation portion of the flexible electrode are located in a hollow portion of the conduit kit to ensure that the electrode sites contact the peripheral nerves after implantation; and a biocompatible adhesive is applied to a portion (such as the outer annular portion) of the implantation portion that contacts the conduit kit for protection and fixation. In addition, the implantation of the flexible electrode may also include one or more steps such as welding the back-end portion of the flexible electrode to the back-end circuit, packaging the back-end portion together with the back-end circuit, applying a high-viscosity waterproof glue to the gap in the package of the back-end portion and the back-end circuit, and applying a biocompatible adhesive to the neck of the flexible electrode.

In an embodiment according to the present disclosure, the conduit kit for assisting implantation may be a Cuff electrode with electrode sites arranged on an inner side thereof, for example, a plurality of parallel metal wire loops may be fixed on the inner side of the Cuff electrode. When the flexible electrode is implanted, the Cuff electrode may be configured to sleeve the surface of the peripheral nerve in an open/close fashion, so that the Cuff electrode can be used to record the local field potential signal outside the nerve bundle while the action potential signal of a single nerve fiber in the nerve bundle is recorded by the flexible electrode. In an embodiment according to the present disclosure, the conduit kit for assisting implantation may also be a silicone tube with good flexibility and elasticity, etc.

Figure 8:
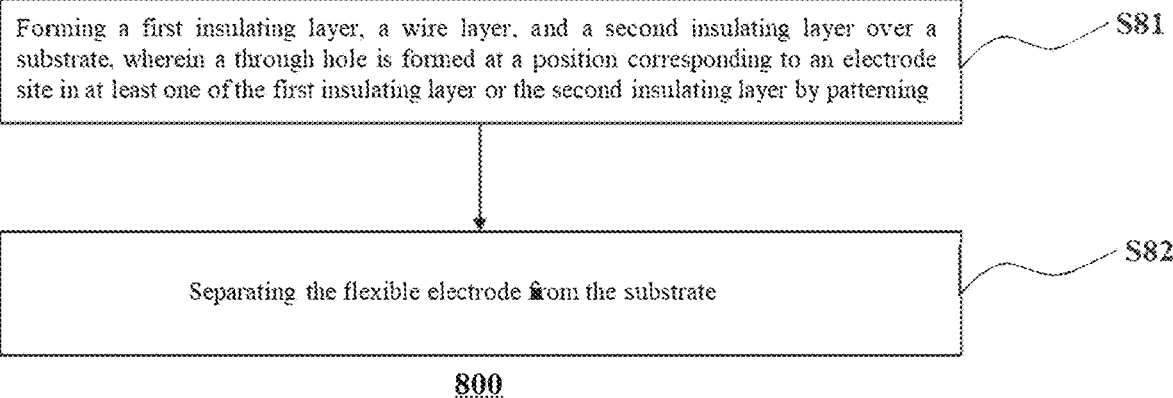
FIG. 8 shows a flowchart of a method for manufacturing a flexible electrode for a peripheral nerve according to an embodiment of the present disclosure.

FIG. 8 shows a flowchart of a method 800 for manufacturing a flexible electrode according to an embodiment of the present disclosure. In the present disclosure, a manufacturing method based on a micro-electro mechanical system (MEMS) process may be adopted to manufacture a nano-scale flexible electrode. As shown in FIG. 8, the method 800 may include: at S81, forming a first insulating layer, a wire layer, and a second insulating layer over a substrate, wherein a through hole is formed at a position corresponding to an electrode site in at least one of the first insulating layer or the second insulating layer by patterning; and at S82, separating the flexible electrode from the substrate. The steps of forming the layers of the flexible electrode at S81 are described in detail below in conjunction with FIG. 9.

Figure 9:
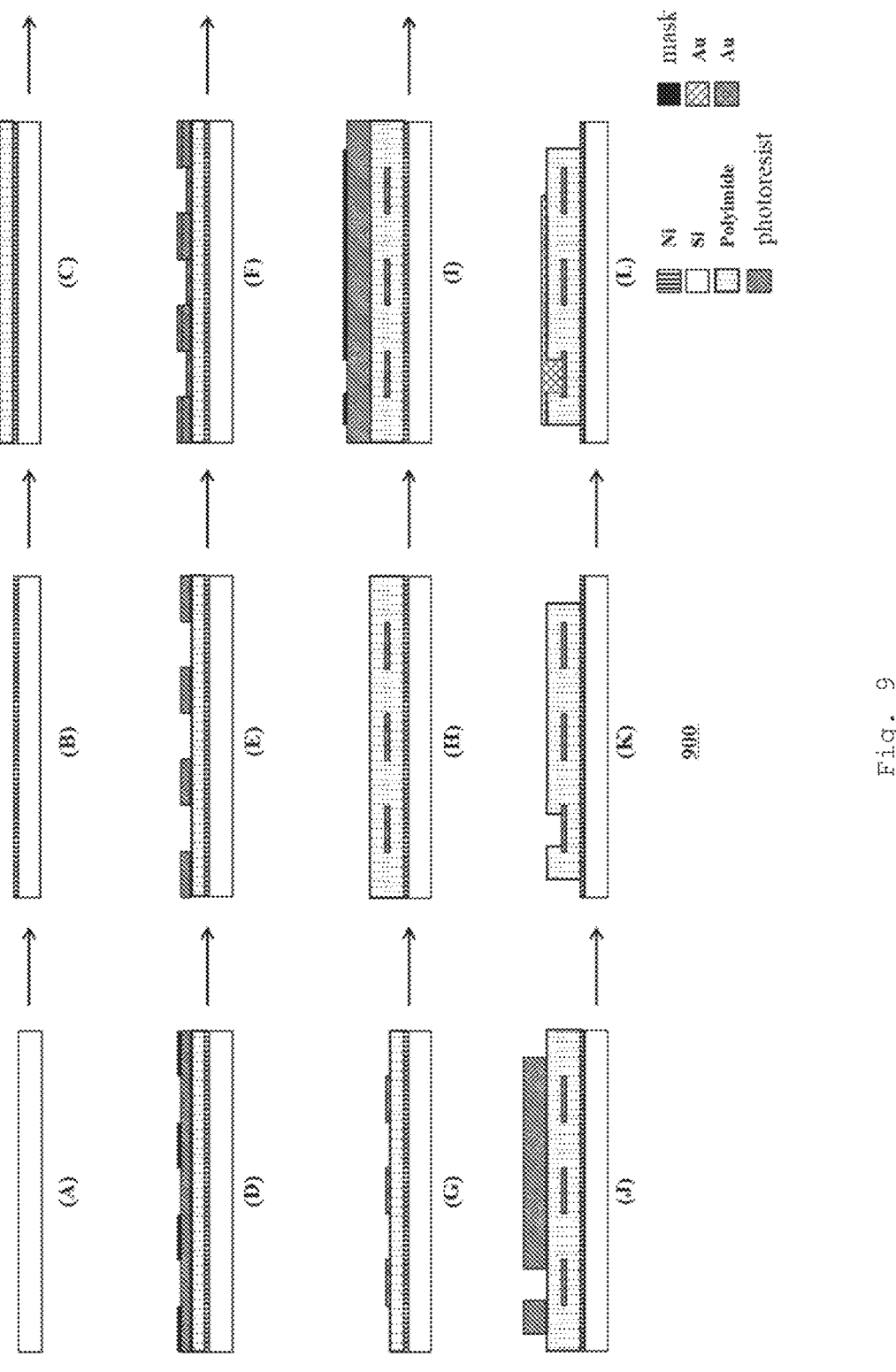
FIG. 9 shows a schematic diagram of a method for manufacturing a flexible electrode for a peripheral nerve according to an embodiment of the present disclosure.

FIG. 9 is a schematic diagram of a method 900 for manufacturing a flexible electrode according to an embodiment of the present disclosure. The forming process and structures of the flexible separation layer, bottom insulating layer, wire layer, top insulating layer, electrode site layer, etc., of the flexible electrode are described in more detail in conjunction with FIG. 9.

The view (A) of FIG. 9 shows a substrate of the electrode. In an embodiment according to the present disclosure, a hard substrate such as glass, quartz, silicon wafer, etc., may be used. In an embodiment according to the present disclosure, other soft materials may also be used as the substrate, such as the same material as that of the insulating layer.

The view (B) of FIG. 9 shows a step of forming a flexible separation layer on the substrate. The flexible separation layer may be removed by applying a specific substance, so as to facilitate the separation of the flexible portion of the electrode from the hard substrate. In the embodiment shown in FIG. 9, Ni is used as the material of the flexible separation layer, and other materials such as Cr and Al may also be used. In an embodiment according to the present disclosure, when a flexible separation layer is formed on the substrate by evaporation, a portion of the exposed substrate may be etched first to improve the flatness of the entire substrate after evaporation. It should be understood that the flexible separation layer is an optional part but not a necessary part of the flexible electrode. Depending on the characteristics of the selected material, the flexible electrode may also be conveniently separated without the flexible separation layer. In an embodiment according to the present disclosure, the flexible separation layer may also be provided with a mark which may be used for alignment of subsequent layers.

The view (C) of FIG. 9 shows forming a bottom insulating layer on the flexible separation layer. As a non-limiting example, in the case where the insulating layer is made of the polyimide material, the forming of the bottom insulating layer may include steps such as a film forming process, a formed-film curing step, and an enhanced curing to form a thin film as the insulating layer. The film forming process may include applying polyimide on the flexible separation layer, for example, a layer of polyimide may be formed by spin coating in segmented rotational speeds. The formed-film curing may include gradually heating to a high temperature and keeping the temperature to form a film, so as to perform subsequent processing steps. The enhanced curing may include multi-gradient temperature increasing before forming subsequent layers, preferably in a vacuum or nitrogen atmosphere, and baking for several hours. It should be understood that the above forming process is only a non-limiting example of the forming process of the bottom insulating layer, and one or more of the steps may be omitted, or more other steps may be included.

It should be noted that the above forming process is directed to an embodiment where a bottom insulating layer is formed in a flexible electrode without a bottom electrode site layer and there is no through hole corresponding to the electrode sites in the bottom insulating layer. If the flexible electrode includes a bottom electrode site layer, the bottom electrode site layer may be formed on the flexible separation layer before forming the bottom insulating layer. For example, Au and Ti may be sequentially evaporated on the flexible separation layer. The step of patterning the bottom electrode sites will be described in detail later with respect to the top electrode sites. Accordingly, in the case where the flexible electrode includes bottom electrode sites, in the process of forming the bottom insulating layer, in addition to the above steps, a patterning step may also be included for etching through holes at positions corresponding to the bottom electrode sites in the bottom insulating layer. The step of patterning the insulating layer will be described in detail later with respect to the top insulating layer.

Views (D) to (G) of FIG. 9 show forming a wire layer on the bottom insulating layer. As shown in the view (D), a photoresist and a mask may be applied on the bottom insulating layer. It should be understood that other photolithography methods may also be used to prepare the patterned thin film, such as laser direct writing and electron beam photolithography. In an embodiment according to the present disclosure, for a metal film such as the wire layer, a double-layer photoresist may be applied to facilitate the forming (evaporation or sputtering) and stripping of the patterned thin film. By providing the pattern of the mask related to the wire layer, for example, the pattern of the wire layer described above may be achieved, such as the patterns of the wire layer 103 of FIG. 1 and the wire layer 403 of FIG. 4. Then, exposure and development may be performed to obtain a structure as shown in the view (E). In an embodiment according to the present disclosure, the exposure may be carried out by contact photolithography, and the mask and the structure are exposed in a vacuum contact mode. This step may also include alignment between the layers. Next, a film may be formed on the structure shown in the view (E), for example, processes such as evaporation and sputtering may be used to deposit a metal thin film material, such as Au, to obtain a structure shown in the view (F). Next, stripping may be performed to separate the thin film in the non-patterned area from the thin film in the patterned area by removing the photoresist in the non-patterned area, so as to obtain a structure as shown in the view (G), that is, to form a wire layer. In an embodiment according to the present disclosure, a photoresist removal may be performed again after the photoresist stripping, so as to further remove the residual photoresist on the surface of the structure.

In an embodiment according to the present disclosure, a back-end site layer may also be formed before forming the wire layer. As a non-limiting example, the forming process of the back-end site layer may be similar to that of the metal film described above with respect to the wire layer.

Views (H) to (K) of FIG. 9 show forming a top insulating layer. For photosensitive thin films, patterning may be generally achieved directly through patterned exposure and development, while for non-photosensitive materials used in the insulating layer, patterning cannot be achieved by exposing and developing the materials themselves. In this case, a sufficiently thick patterned anti-etching layer may be formed on this layer, and then the thin film in an area not covered by the anti-etching layer is removed by dry etching (the anti-etching layer will also be thinned at the same time, so it is necessary to ensure that the anti-etching layer is thick enough), and then the anti-etching layer is removed to achieve the patterning of the non-photosensitive layer. As a non-limiting example, when forming the insulating layer, the photoresist may be used as the anti-etching layer. The forming of the top insulating layer may include steps such as a film forming process, formed-film curing, patterning, and enhanced curing, wherein the view (H) shows a structure obtained after the film-forming of the top insulating layer, the view (I) shows the application of photoresist and mask on the top insulating layer after the film-forming, the view (J) shows a structure including the anti-etching layer obtained after exposure and development, and the view (K) shows a structure including the top insulating layer formed. The film forming process, formed-film curing and enhanced curing have been described in detail above with respect to the bottom insulating layer, and description therefor is omitted here for brevity. The patterning step may be performed after the formed-film curing, or after the enhanced curing. After the enhanced curing, the insulating layer has a stronger anti-etching ability. Specifically, in the view (I), a sufficiently thick layer of photoresist is applied on the insulating layer through steps such as spin coating and baking. By providing the pattern of the mask related to the top insulating layer, for example, the pattern of the top insulating layer 102 shown in FIG. 1 may be realized, that is, the contours of the flexible electrode 100 at the implantation portion 110 (especially the pores included in the implantation portion 110) and the back-end portion 120 and the contours of the through holes implemented at positions corresponding to the electrode sites and the back-end sites in the top insulating layer. In the view (J), the pattern is transferred to the photoresist on the insulating layer through steps such as exposure and development to obtain an anti-etching layer, wherein the portion to be removed from the top insulating layer is exposed. The exposed portion of the top insulating layer may be removed by oxygen plasma etching, and after flood exposure, the remaining photoresist on the top insulating layer is removed with a developer or acetone, etc., to obtain a structure shown in the view (K).

In an embodiment according to the present disclosure, an adhesion enhancement treatment may also be performed before the top insulating layer is formed, so as to improve the bonding force between the bottom insulating layer and the top insulating layer.

The view (L) of FIG. 9 shows forming a top electrode site layer on the top insulating layer.

The manufacturing method 900 shown in FIG. 9 is applicable to the case where the thickness of each layer is the same for respective parts of the flexible electrode. In an embodiment according to the present disclosure, the respective parts of the flexible electrode may have different thicknesses, for example, at least one of the first insulating layer or the second insulating layer in the outer annular portion of the implantation portion may be thickened.

Figure 13:
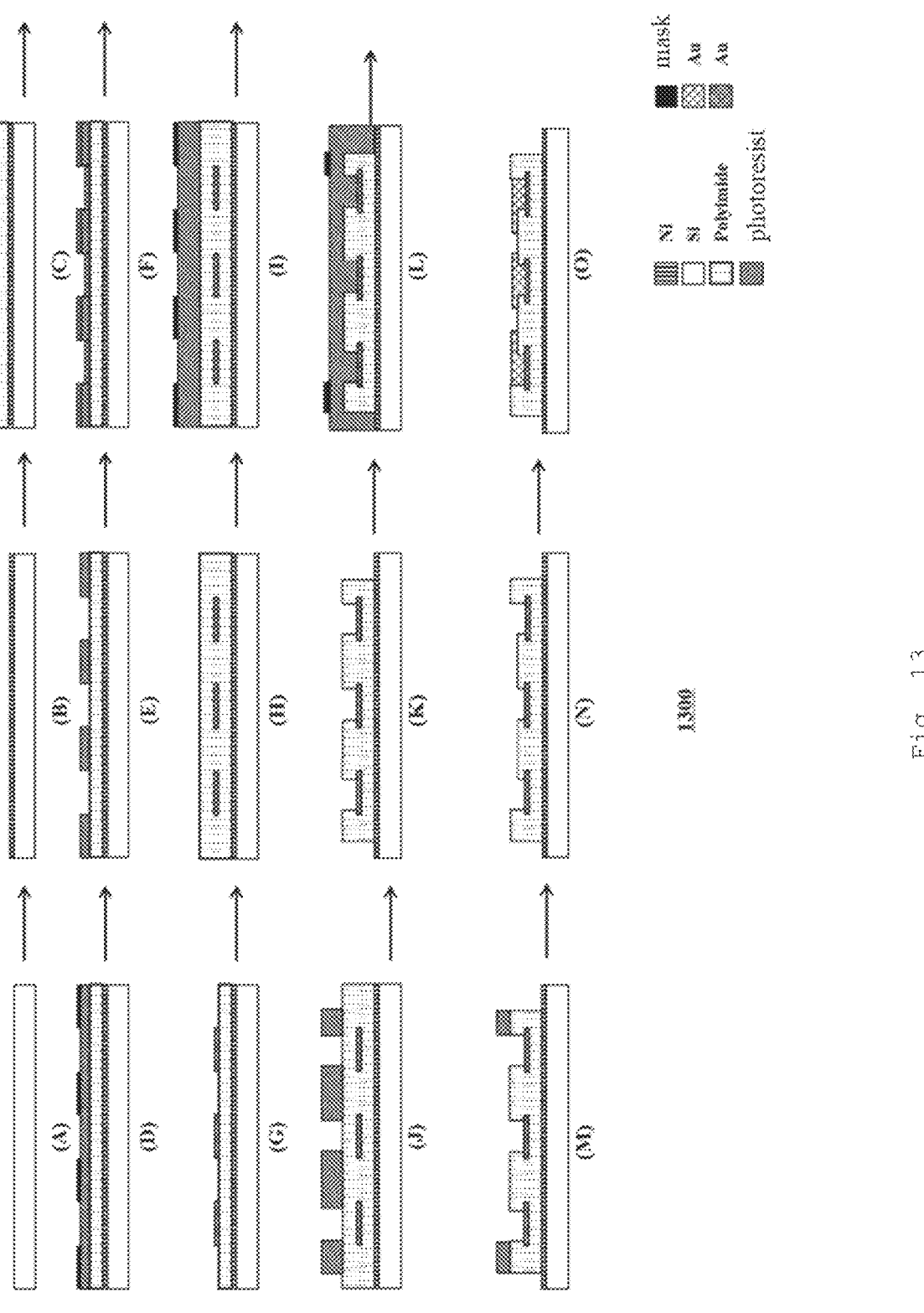
FIG. 13 shows a schematic diagram of a method for manufacturing a flexible electrode for a peripheral nerve according to an embodiment of the present disclosure.

FIG. 13 shows a schematic diagram of a method 1300 for manufacturing a flexible electrode for a peripheral nerve according to an embodiment of the present disclosure. The manufacturing method 1300 shown in FIG. 13 is applicable to the case where the top insulating layer of the outer annular portion is thickened.

Views (A) to (G) of FIG. 13 showing the forming of the flexible separation layer, the bottom insulating layer, and the wire layer are similar to views (A) to (G) of FIG. 9, and are not described again herein.

Views (H) to (K) of FIG. 13 show forming the top insulating layer. For the sake of brevity, those in the forming process of the top insulating layer similar to those of views (H) to (K) of FIG. 5 are not repeated here. In order to make the outer annular portion in the implantation portion have a different thickness from that of the extension portion, the inner annular portion, and the like, the top insulating layer of the outer annular portion is formed thicker here. The view (H) of FIG. 13 shows a structure obtained after the film-forming of the top insulating layer. The view (I) of FIG. 13 shows the application of photoresist and mask on the top insulating layer after the film-forming, wherein the pattern of the mask is set to be related to the top insulating layer, for example, the pattern of the top insulating layer 102 shown in FIG. 1 may be implemented, that is, the contour of the top insulating layer implemented on one or more wires in the electrode extending from the back-end portion and the contours of the through holes implemented at the positions corresponding to the electrode sites in the top insulating layer. The view (J) of FIG. 13 shows a structure including an anti-etching layer obtained after exposure and development. The view (K) of FIG. 13 shows a structure of the top insulating layer after etching, at this time, the top insulating layers of the outer annular portion, the extension portion, the inner annular portion, and the like, have the same thickness. The view (L) of FIG. 13 shows that a photoresist and a mask are applied again on the etched top insulating layer of the view (K), wherein the pattern of the mask is set to be related to the top insulating layer of the outer annular portion, for example, the pattern of the top insulating layer 102 of the outer annular portion shown in FIG. 1 may be implemented. The view (M) of FIG. 13 shows a structure including an anti-etching layer obtained after exposing and developing again, which is located on the insulating layer of the outer annular portion to protect the insulating layer of the outer annular portion and expose the insulating layers of the extension portion, the inner annular portion, and the like. The view (N) of FIG. 13 shows the final top insulating layer obtained after etching, wherein portions of the insulating layers of the extension portion, the inner annular portion, and the like are etched away, so that their thicknesses are less than that of the insulating layer of the outer annular portion.

The view (O) of FIG. 13 shows a top electrode site layer formed on the top insulating layer by evaporation or the like.

The present disclosure provides a flexible electrode for a peripheral nerve and a method for manufacturing the same. For the flexible electrode, a flexible material is used to replace a hard silicon-based electrode, a high molecular polymer is used as an insulating layer to wrap a conductive material, and the thickness of the electrode is reduced to reduce its bending stiffness, thereby ameliorating the mechanical property mismatch between the electrode and the tissue, and ultimately providing a long-term stable interface for electrical signal recording and stimulation. In addition, the flexible electrode is designed with pores, the property of reconstruction of a peripheral nerve is utilized to implant the electrode into two completely truncated nerves, and the active formation of a close electrode-tissue interface between the electrode and the nerve and blood vessel during a repairing process therefor is utilized to achieve signal recording and stimulation.

The words "front", "rear", "top", "bottom", "above", "below", etc., if present, in the specification and claims are used for descriptive purposes and are not necessarily used to describe an invariant relative position. It should be understood that the words so used are interchangeable where appropriate, such that the embodiments of the present disclosure described herein, for example, are capable of operation in other orientations than those illustrated or otherwise described herein.

As used herein, the word "exemplary" means "used as an example, instance, or illustration" rather than serving as a "model" to be exactly copied. Any implementation described as an example herein is not necessarily to be construed as preferred or advantageous over other implementations. Moreover, the present disclosure is not limited by any stated or implied theory given in the above sections of technical field, background, summary, or detailed description.

As used herein, the term "substantially" is intended to include any minor variations due to design or manufacturing imperfections, device or component tolerances, environmental influences, and/or other factors. The term "substantially" also allows for deviations from a perfect or ideal situation due to parasitic effects, noise, and other practical considerations that may exist in actual implementations.

The terms "first", "second" and the like may be used herein for reference purposes only and are not intended to be limiting. For example, the terms "first", "second" and other such numerical terms referring to structures or elements do not imply a sequence or order unless the context clearly indicates otherwise.

It should also be understood that when the term "include/comprise" is used herein, it indicates the presence of the stated features, entities, steps, operations, units and/or components, but does not exclude the presence or addition of one or more other features, entities, steps, operations, units and/or components and/or combinations thereof.

As used herein, the term "and/or" includes any and every combinations of one or more of the associated listed items. The terms used herein are for the purpose of describing specific embodiments only and are not intended to limit the present disclosure. As used herein, the singular forms "a", "an", and "the" are also intended to include the plural forms, unless the context clearly indicates otherwise.

Those skilled in the art will appreciate that the boundaries between the above operations are merely illustrative. Multiple operations may be combined into a single operation, a single operation may be distributed in additional operations, and operations may be performed at least partially overlapping in time. Moreover, alternative embodiments may include multiple instances of a particular operation, and the operation order may be changed in other various embodiments. However, other modifications, variations, and replacements are also possible. Therefore, this specification and accompanying drawings should be considered illustrative, not restrictive.

Although some specific embodiments of the present disclosure have been described in detail by way of example, it should be understood by those skilled in the art that the above examples are for illustration only and are not intended to limit the scope of the present disclosure. The various embodiments disclosed herein may be combined in any manner without departing from the spirit and scope of the present disclosure. It should also be understood by those skilled in the art that various modifications may be made to the embodiments without departing from the scope and spirit of the present disclosure. The scope of the present disclosure is defined by the appended claims.

What is claimed is:

1. A flexible electrode for a peripheral nerve, the flexible electrode comprising an implantation portion that is capable of being implanted into a truncated peripheral nerve or a nerve stump, wherein:

the flexible electrode comprises a first insulating layer, a second insulating layer, and a wire layer located between the first insulating layer and the second insulating layer;

the implantation portion comprises one or more electrode sites, each of which is electrically coupled to one of wires in the wire layer, and is in contact with the peripheral nerve after implantation of the flexible electrode to acquire an electrical signal from the peripheral nerve and transmit the acquired electrical signal via the wire, or to apply a stimulation electrical signal received via the wire to the peripheral nerve; and the implantation portion has pores to facilitate reconstruction of the peripheral nerve and to be in close contact with the peripheral nerve after the reconstruction, wherein the implantation portion comprises an outer annular portion and one or more extension portions extending inwards respectively from the outer annular portion, wherein the one or more extension portions and the annular portions are adapted to be disposed internal to the truncated peripheral nerve or the nerve stump, wherein the annular portion defines a plane that is parallel to a cross-sectional area of the truncated peripheral nerve or the nerve stump, the one or more electrode sites are located on the one or more extension portions, and a respective wire in the wire layer extends to a corresponding one of the electrode sites along at least a portion of the outer annular portion and one of the one or more extension portions.

2. The flexible electrode according to claim 1, wherein the one or more extension portions extend linearly inwards respectively;

an inner portion of the implantation portion is configured to be capable of being deformed or at least partially disconnected from the implantation portion during the reconstruction of the peripheral nerve after the implantation.

3. The flexible electrode according to claim 1, wherein the one or more extension portions are applied with a biocompatible adhesive during packaging; or the outer annular portion of the implantation portion is thickened; or the extension portion has a shape of a horseshoe, a wheel, a belt, a strip or a mesh; or the flexible electrode comprises a plurality of wire layers which are separated by an additional insulating layer therebetween, and each of the wire layers comprises therein a plurality of wires spaced apart from each other;

the electrode site is shaped as required, a number of the electrode sites is one or more, a maximum side length or diameter of the electrode site is 1 micron to 500 microns, a spacing between the electrode sites is 10 microns to 10 millimeters, and a thickness of the electrode site is 5 nanometers to 200 microns; or the first insulating layer and the second insulating layer have a thickness of 100 nanometers to 300 micrometers; or a material of the first insulating layer and the second insulating layer is any one of polyimide, polydimethylsiloxane, parylene, epoxy resin, polyamide imide, SU-8 photoresist, silica gel, silicone rubber, or a combination thereof; or the pores are shaped and sized according to a size of the peripheral nerve, and porosity of the implantation portion is greater than 70%; or a material of the wire layer is any one of magnesium, molybdenum or alloys thereof or a combination thereof, and a material of the first insulating layer and the second insulating layer is any one of polylactic acid or polylactic acid-glycolic acid copolymer or a combination thereof, so that the flexible electrode is biodegradable.

4. The flexible electrode according to claim 1, wherein:

the electrode site is located outside at least one of the first insulating layer or the second insulating layer, and is electrically coupled to the wire in the wire layer via a through hole in the at least one of the first insulating layer or the second insulating layer.

5. The flexible electrode according to claim 4, wherein a material of the electrode site is any one of gold, platinum, iridium, tungsten, magnesium, molybdenum, platinum-iridium alloy, titanium alloy, graphite, carbon nanotubes, PEDOT or a combination thereof; or the electrode site is located in the wire layer and is exposed via a through hole in at least one of the first insulating layer or the second insulating layer.

6. The flexible electrode according to claim 4, wherein the electrode site comprises a conductive sub-layer, and a material of the conductive sub-layer is any one of gold, platinum, iridium, tungsten, magnesium, molybdenum, platinum-iridium alloy, titanium alloy, graphite, carbon nanotubes, PEDOT or a combination thereof.

7. The flexible electrode according to claim 6, wherein the electrode site further comprises an adhesion sub-layer close to the wire layer, the adhesion sub-layer being made of a material capable of enhancing adhesion between the electrode site and the wire layer.

8. The flexible electrode according to claim 1, further comprising a back-end portion to be implanted subcutaneously, wherein:

the implantation portion extends from the back-end portion, and the back-end portion comprises a back-end site coupled to a back-end circuit and one of the wires in the wire layer to achieve bidirectional signal transmission between the back-end circuit and the electrode site electrically coupled to the one of the wires.

9. The flexible electrode according to claim 8, wherein the back-end site is located in the wire layer and is exposed via a through hole in at least one of the first insulating layer or the second insulating layer; or the wire layer comprises a conductive sub-layer and an adhesion sub-layer close to any one of the electrode sites or the back-end site, and a material of the adhesion sub-layer is any one of chromium, tantalum, tantalum nitride, titanium, titanium nitride or a combination thereof.

10. The flexible electrode according to claim 8, wherein the back-end site is located between the wire layer and at least one of the first insulating layer or the second insulating layer, and is electrically coupled to the wire in the wire layer.

11. The flexible electrode according to claim 10, wherein the back-end site comprises a conductive sub-layer, and a material of the conductive sub-layer is any one of gold, platinum, iridium, tungsten, magnesium, molybdenum, platinum-iridium alloy, titanium alloy, graphite, carbon nanotubes, PEDOT or a combination thereof; or the back-end site has a thickness of 5 nanometers to 200 micrometers; or the back-end site further comprises an adhesion sub-layer close to the wire layer, and a material of the adhesion sub-layer is any one of chromium, tantalum, tantalum nitride, titanium, titanium nitride or a combination thereof.

12. The flexible electrode according to claim 8, wherein after the flexible electrode is separated from a substrate, the back-end portion is connected to the back-end circuit, and the back-end portion and the back-end circuit are packaged together by any one of epoxy resin or polydimethylsiloxane or a combination thereof.

13. The flexible electrode according to claim 12, wherein a gap in a package of the back-end portion and the back-end circuit is applied with a high-viscosity waterproof glue; or a neck of the flexible electrode between the implantation portion and the back-end portion is applied with a biocompatible adhesive.

14. The flexible electrode according to claim 1, wherein when implanting the flexible electrode, a portion of the implantation portion that is in contact with a conduit kit for assisting implantation is applied with a biocompatible adhesive;

wherein when implanting the flexible electrode, the conduit kit is fixed to the truncated peripheral nerve and the implantation portion is located between cross sections of the conduit kit.

15. The flexible electrode according to claim 14, wherein the conduit kit for assisting implantation is a cuff electrode with electrode sites arranged on an inner side thereof; when implanting the flexible electrode, the cuff electrode is configured to sleeve the surface of the peripheral nerve in an open/close fashion, so that the cuff electrode is used to record a local field potential signal outside the nerve bundle while the flexible electrode is used to record an action potential signal of a single nerve fiber in the nerve bundle; or the conduit kit for assisting implantation is a flexible and elastic silicone tube.

16. The flexible electrode according to claim 1, wherein the wire layer comprises a conductive sub-layer, and a material of the conductive sub-layer is any one of gold, platinum, iridium, tungsten, platinum-iridium alloy, titanium alloy, graphite, carbon nanotubes, PEDOT or a combination thereof.

17. The flexible electrode according to claim 16, wherein the conductive sub-layer has a thickness of 5 nanometers to 200 micrometers.

18. The flexible electrode according to claim 1, further comprising a flexible separation layer, wherein the flexible separation layer is capable of being removed by a substance to separate a part of the flexible electrode without damage to the flexible electrode.

19. The flexible electrode according to claim 18, wherein a material of the flexible separation layer is any one of nickel, chromium, aluminum, or a combination thereof; or the flexible separation layer further comprises an adhesion sub-layer, and a material of the adhesion sub-layer is chromium, tantalum or titanium.

20. A method for manufacturing a flexible electrode for a peripheral nerve according to claim 1, comprising:

forming the first insulating layer, the wire layer, the second insulating layer, and the electrode site over a substrate; and separating the flexible electrode from the substrate, wherein a through hole is formed at a position corresponding to the electrode site in at least one of the first insulating layer or the second insulating layer by patterning.

\* \* \* \* \*